US011887710B2

(12) United States Patent
Khan et al.

(10) Patent No.: US 11,887,710 B2
(45) Date of Patent: Jan. 30, 2024

(54) PRECISION-BASED IMMUNO-MOLECULAR AUGMENTATION (PBIMA) COMPUTERIZED SYSTEM, METHOD, AND THERAPEUTIC VACCINE

(71) Applicant: Neo7Logix, LLC, Dallas, TX (US)

(72) Inventors: Shamsuddin Sultan Khan, Dhaka zila (BD); John A. Catanzaro, Rockwall, TX (US); Anton Yuryev, Gaithersburg, MD (US)

(73) Assignee: Neo7Logix, LLC

( * ) Notice: Subject to any disclaimer, the term of this patent is extended or adjusted under 35 U.S.C. 154(b) by 0 days.

(21) Appl. No.: 17/944,335

(22) Filed: Sep. 14, 2022

(65) Prior Publication Data

US 2023/0146516 A1  May 11, 2023

Related U.S. Application Data

(63) Continuation of application No. PCT/US2021/022858, filed on Mar. 17, 2021.

(60) Provisional application No. 63/029,633, filed on May 25, 2020, provisional application No. 62/992,227, filed on Mar. 20, 2020.

(51) Int. Cl.
*G16H 10/60* (2018.01)
*G16H 10/40* (2018.01)
*G16B 50/20* (2019.01)
*G16B 20/00* (2019.01)

(52) U.S. Cl.
CPC ............. *G16H 10/60* (2018.01); *G16B 20/00* (2019.02); *G16B 50/20* (2019.02); *G16H 10/40* (2018.01)

(58) Field of Classification Search
CPC ........ G16H 10/60; G16H 10/40; G16B 50/20; G16B 20/00
USPC ....................................................... 705/2–3
See application file for complete search history.

(56) References Cited

U.S. PATENT DOCUMENTS

| | | | |
|---|---|---|---|
| 2017/0037154 A1* | 2/2017 | Jung | A61K 39/001106 |
| 2017/0290897 A1* | 10/2017 | Mahr | C07K 14/001 |
| 2018/0291083 A1* | 10/2018 | Walz | C07K 14/7051 |
| 2019/0135902 A1* | 5/2019 | Gelfand | C07K 16/28 |
| 2020/0087364 A1* | 3/2020 | Schuster | A61K 39/001152 |

(Continued)

*Primary Examiner* — Michael Tomaszewski
(74) *Attorney, Agent, or Firm* — Caldwell Intellectual Property Law

(57) ABSTRACT

As disclosed herein a precision based immunomolecular augmentation (PBIMA) high specificity patient profiling networked computer system, rapid therapeutic vaccine design method, and personalized vaccine, which utilizes immuno-molecular biopathway HLA affinity mapping and selection prediction ranking tools. This PBIMA approach comprises: Strategic-Selection, Molecular-Mapping, Antigen-Alignment, Receptor-Recognition, and Tactical Technology (SMART). The platform obtains data from a patient's genes and proteins as input. NGS data, including WES, WGS, ctDNA and cfDNA, RNAseq uses as input. PBIMA comprises a gene-protein-cell Cloud-based sequence editing interface to select the high confidence peptides. The PBIMA vaccine is a solution-based multi-purpose vaccine design strategy. PBIMA technology can produce therapeutic vaccines for cancer, autoimmune, neurodegenerative, inflammation-driven disease, and novel pathogen infection treatment. PBIMA therapeutic design is multi-mechanistic and broad-spectrum.

19 Claims, 6 Drawing Sheets

Specification includes a Sequence Listing.

(56) References Cited

U.S. PATENT DOCUMENTS

2020/0188438 A1\* 6/2020 Schimmack ........... A61K 35/17
2020/0276289 A1\* 9/2020 Rubsamen ........... C12Q 1/6886

\* cited by examiner

PRECISION-BASED IMMUNO-MOLECULAR AUGMENTATION (PBIMA) COMPUTERIZED SYSTEM, METHOD, AND THERAPEUTIC VACCINE

CROSS-REFERENCE TO RELATED APPLICATIONS

This application is a continuation of International Application published under the Patent Cooperation Treaty No. WO 2021/188743 A3 filed on Mar. 17, 2021 and entitled "PRECISION-BASED IMMUNO-MOLECULAR AUGMENTATION (PBIMA) COMPUTERIZED SYSTEM, METHOD AND THERAPEUTIC VACCINE" the entirety of which is incorporated herein by reference.

REFERENCE TO AN ELECTRONIC SEQUENCE LISTING

The contents of the electronic sequence listing (sequence listing.xml; 22,550 bytes; and Date of Creation: Jan. 16, 2023) is hereby incorporated by reference in its entirety.

FIELD OF THE INVENTION

The present invention generally relates to the field of cloud-based biopathway human leukocyte antigen (HLA) affinity mapping and a selection prediction ranking method. In particular, the present invention is directed to precision-based immune-molecular augmentation (PBIM) computerized system, method and therapeutic vaccine.

BACKGROUND

Malignant tumors are associated with high morbidity and mortality rates with a reported 18.1 million new cases of cancer and 9.6 million cancer-related deaths in 2018 (Bray et al., 2018). Importantly, malignant cell transformation links with the accumulation of DNA damage. Over the past years, research has shown that the immune system, specifically T-cells, can respond to neo-antigens that arise due to this DNA damage (Peng et al., 2019). Of note, neo-antigens are proteins whose genes are somatically mutated in patient tumors and expressed in tumor cells (Efremova et al., 2017). These differ from self-antigens, or non-mutated proteins, that overexpresses in tumor cells. As such, neo-antigens are used to direct the immune response towards cancer cells directly, thus minimizing the risk of developing an autoimmune reaction against a patient's healthy tissue (Shujing et al., 2015). On the other hand, self-antigens are used as adjuvants to boost the immune response and increase the immunity's duration, thus minimizing the dose of antigen needed (Guo et al., 2018, Khong et al., 2016). The best self-antigens are the proteins whose expression is upregulated in tumor cells compared to normal cells (Yarchoan et al., 2017).

Studies have shown that the recognition of neo-antigens is an essential driver of the clinical efficacy for standard-of-care cancer immunotherapies, whether via T-cell checkpoint blockade and adoptive T-cell therapy (CAR-T) (Yarchoan et al., 2017, Peng et al., 2019). The relevance of personalized neo-antigens in tumor control and these antigens' biological properties has been extensively studied (Yuryev and Catanzaro, 2019). Crucially, recent technological advances utilizes to identify novel neo-antigens and isolate T-cells that recognize them in individual patients (Yuryev et al., 2019a, Peng et al., 2019). This personalized neo-antigen design can be then employed in clinical interventions (Yuryev et al., 2019b).

Previously, neo-antigens were ignored as cancer immunotherapy targets due to their enormous diversity, as this was a limitation for developing "one fits all" pharmacologic solution. However, the advent of the personalized medicine paradigm that does not fit the "one fits all" pharmacologic solution schema rekindled using neo-antigen vaccines for personalized immunotherapy. This medicine style is changing the landscape of medical practice, but it requires a more sophisticated precision for personalized cancer vaccines (Catanzaro and Dickens, 2019). In recent years, several clinical trials demonstrated that neo-antigens could facilitate response to checkpoint inhibition (Guo et al., 2018), thus dramatically altering our view on the clinical potential of neo-antigens in cancer immunotherapy.

Technological advances, such as whole-genome sequencing, whole cancer exomics, RNA tumor transcriptomics, and proteomics, develop reliable algorithms for epitope prediction. An increasing number of immunotherapeutic options now facilitate personalized cancer therapies directly targeting a patient's tumor (Yuryev and Catanzaro, 2019, Yuryev and Castillos, 2016, Anastasia et al., 2019, Antunes et al., 2018). Integration of artificial intelligence, machine learning, knowledge graph methods, literature correlation/bioinformatics, and biophysical computation enable first-principles precision science to predict personalized neo-antigen design. In fact, the relevance of personalized neo-antigens in tumor control and the antigens' biological properties has been extensively determined in several disease states by many other groups and us. Indeed, the PBIMA technology has directly shown the ability of this technique to target various diseases.

Moreover, designing a PBIMA vaccine using antimicrobial and anti-viral pooled peptides will influence and induce the immune response against the pathogen. Therefore, viruses, bacteria, fungus, parasites, and whatsoever can not enter, replicate, and get involved with actual protein encoding interference so that the infected cells will die quicker. At the same time, these pooled peptides can also control the prevention of an inflammatory crisis in the patient that often leads to a severe inflammation reaction. In these cases, the patients die from extensive inflammatory moieties because of inflammation caused by a novel coronavirus. The PBIMA vaccine is a solution-based vaccine design approach that will address the infectious disease objectively on the knowledge of how the human immune interaction happens, rather than addressing it subjectively as a science of the pathogen. This kind of vaccine will have high specificity with broad activity to various people because of its SMART mechanism of action.

Human history has experienced significant pandemics such as smallpox, cholera, plague, dengue, AIDS, influenza, severe acute respiratory syndrome (SARS), West Nile disease, and tuberculosis. Influenza pandemics were sporadic yet frequent phenomena in the last decades. Each pandemic harmed human life and economic growth. It is an epidemic danger made more apparent by the number of new emerging infectious diseases. The World Health Organization is considering developing a pipeline partnership to design a rapid vaccine to prevent this series of pandemic crises. No platform technology is available yet to create a safe and effective therapeutic vaccine, especially one using pathogen identification (but not limited to bacteria, virus, and fungi) antigens for CD4+/CD8+ cell modulation. Developing this kind of technology is an emerging requirement, and a designed approach for a multi-platform development to create a therapeutic vaccine is needed.

SUMMARY OF THE DISCLOSURE

In an aspect, a precision-based immunomolecular augmentation (PBIMA) computerized method for designing and treating a patient with a customized therapeutic peptides or peptide vaccine, comprising receiving a data input, by a cloud-based system, of a patient data comprising one or more of: a patient transcriptomics data, and a patient urine proteomics data; computing a precision data output, by the cloud-based system, of a vaccine composition comprising a plurality of ranked peptide sequences encoding self-antigens and/or neo-antigens for a CD4+/CD8+ natural killer (NK) cell modulation specific to a patient's profile, and able to elicit an effective therapeutic response against a patient disease; computing a CRISPR prime editing and an intracellular multi-core processing on the vaccine composition to produce a DNA-RNA and epigenetic modulation plurality of immunopeptide sequences; conducting an immunopeptide synthesis and manufacturing of the vaccine composition; conducting the delivery of the vaccine composition to a patient's clinician or institution, and administrating the vaccine composition to the patient; and wherein the patient has been diagnosed with, and/or is genetically predisposed to one or more diseases comprising: a cancer, an autoimmune disease, a neurodegenerative disease, and/or a pathogenic infectious disease.

In another aspect, A cloud-based computer system able to design a personalized peptide vaccine, comprising: a precision based immunomolecular augmentation (PBIMA) computing platform comprising a plurality of online databases and application program interfaces (APIs), and comprising non-transitory computer readable storage medium storing computer-executable code comprising all of a next-generation sequencing (NGS) OMICS file processing unit comprising a Blood and RNA tumor VCF file, a WES VCF file, and a urine Proteomics data excel file; a Peptide Analysis Tool comprising an open-source database and an online API; a Susceptibility Tool comprising an open-source database and an online API; a Genome Uniqueness comprising an open-source database and an online API; a Gene-Protein-Disease Interaction Database comprising an open-source or proprietary database and an online API; a Sequence Integrity module comprising an open-source database and online API, Thermofisher, Dosorio R package); PBIMA Unification API (Neo7Logix Cloud base integrative API) to design and rank neoantigens of the 9-aminoacid peptides-MHC-I, and 12-aminoacid peptides-MHC-II; a Payload API to match the best payloads for delivery for a more specific targeted delivery; a plurality of local and/or remote computers able to transmit patient input data to a PBIMA editing system, the input data comprising: NGS, WES, RNAseq, circulating DNA (ctDNA and cfDNA) and Urine proteomics data; a wired and/or wireless network connecting local and/or remote computers' plurality; wherein a patient has been diagnosed with, or is genetically predisposed to, a disease comprising: a cancer, an autoimmune disease, a neurodegenerative disease, or a pathogen related infectious disease; and wherein the personalized peptide vaccine comprises a plurality of peptide sequences comprising about 5 to about 20 peptide sequences computed to be the most therapeutically effective peptide for treating the patient by eliciting a CD4+/CD8+NK cell modulation specific to a patient's profile.

The details of one or more variations of the subject matter described herein are set forth in the accompanying drawings and the description below. Other features and advantages of the subject matter described herein will be apparent from the description and drawings, and from the claims.

For the purpose of illustrating the invention, the drawings show aspects of one or more embodiments of the invention. However, it should be understood that the present invention is not limited to the precise arrangements and instrumentalities shown in the drawings, wherein: FIG. 1A is a block diagram illustrating an exemplary embodiment of computer system architecture illustrating the PBIMA Cloud-based sequence editing API and treatment method for patient data acquisition using an internet-based system. The computational pipeline is for PBIMA design, immunopeptide synthesis and manufacturing, PBIMA delivery, and administration into patients;

The drawings are not necessarily to scale and may be illustrated by phantom lines, diagrammatic representations, and fragmentary views. In certain instances, details that are not necessary for an understanding of the embodiments or that render other details difficult to perceive may have been omitted. Like reference symbols in the various drawings indicate like elements.

DETAILED DESCRIPTION

This application contains a sequence listing, which is submitted electronically via EFS-Web as an XML formatted sequence listing with a file name "sequence listing", creation date of Sep. 13, 2022, and having a size of about 22.0 kilobytes. The sequence listing that is filed concurrently via EFS-Web is part of the specification and is herein incorporated by reference in its entirety.

Figure 1A:
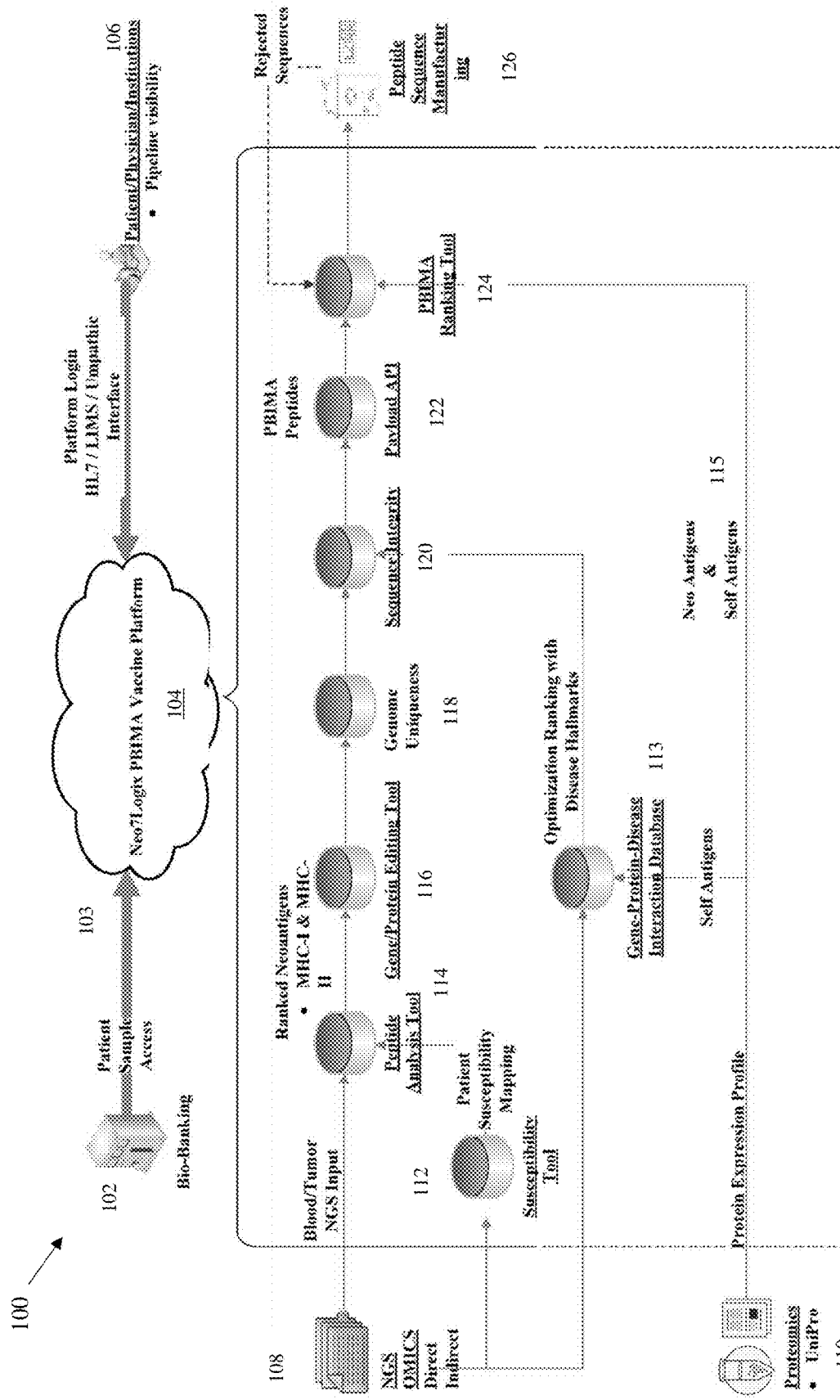
FIG. 1B is a diagram illustrating the PBIMA Application method-input and output.

Referring now to FIG. 1A, an exemplary embodiment of precision-based immune-molecular augmentation (PBIMA) computerized system is illustrated. System includes a cloud-based computer system. Cloud-based computer system may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Cloud-based computer system may include a single computing device operating independently, or may include two or more computing device operating in concert, in parallel, sequentially or the like; two or more computing devices may be included together in a single computing device or in two or more computing devices. Cloud-based computer system may interface or communicate with one or more additional devices as described below in further detail via a network interface device. Network interface device may be utilized for connecting cloud-based computer system to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Cloud-based computer system may include but is not limited to, for example, a computing device or cluster of computing devices in a first location and a second computing device or cluster of computing devices in a second location. Cloud-based computer system may include one or more computing devices dedicated to data storage, security, distribution of traffic for load balancing, and the like. Cloud-based computer system may distribute one or more computing tasks as described below across a plurality of computing devices of computing device, which may operate in parallel, in series, redundantly, or in any other manner used for distribution of tasks or memory between computing devices. Cloud-based computer system may be implemented using a "shared nothing" architecture in which data is cached at the worker, in an embodiment, this may enable scalability of system 100 and/or computing device.

With continued reference to FIG. 1A, cloud-based computer system may be designed and/or configured to perform any method, method step, or sequence of method steps in any embodiment described in this disclosure, in any order and with any degree of repetition. For instance, cloud-based computer system may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Cloud-based computer system may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1A, Precision-Based Immuno-Molecular Augmentation (PBIMA) computerized method, system, and peptide vaccine compositions comprises high specificity patient profiling that requires a Cloud-based API system. This Cloud system utilizes immuno-molecular biological pathways and HLA affinity mapping, prediction and ranking obtained from patient's genomics and proteomics data for personalized cancer vaccine design. As used in this disclosure, a "PBIMA" refers to precision-based Immuno-Molecular Augmentation, which is a patient customized vaccine composition and treatment protocol, comprising an immune sequence design aimed at correcting faults, initiating or regulating pathways as revealed by the patient's own biological data derived from patient tissue, blood, tumor, and or urine samples, that needs correction or enhancement.

With continued reference to FIG. 1A, as used in this disclosure, terms "including", "comprising" or "having" and variations thereof herein is meant to encompass the items listed thereafter and equivalents thereof, as well as additional items. As used in this disclosure, terms "a" and "an" herein do not denote a limitation of quantity, but rather denote the presence of at least one of the referenced items. Further, as used in this disclosure, terms "first", "second", and "third", and the like, herein do not denote any order, quantity, or importance, but rather are used to distinguish one element from another. As used in this disclosure, the term "about" refers to plus or minus the stated amount.

With continued reference to FIG. 1A, as used in this disclosure, the transitional term "comprising", which is synonymous with "including," "containing," or "characterized by," is inclusive or open-ended and does not exclude additional, unrecited elements or method steps. As used in this disclosure, the transitional phrase "consisting of" excludes any element, step, or ingredient not specified in the claim. As used in this disclosure, the transitional phrase "consisting essentially of" limits the scope of a claim to the specified materials or steps "and those that do not materially affect the basic and novel characteristic(s)" of the claimed invention.

With continued reference to FIG. 1A, as used in this disclosure, the term "about" refers to 5, 6, 7, 8, 9, or 10 percent plus and/or minus the stated amount.

With continued reference to FIG. 1A, as used in this disclosure, the term "module" may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

With continued reference to FIG. 1A, as used in this disclosure, the term "computer-executable code" may include software, firmware, and/or microcode and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

With continued reference to FIG. 1A, as used in this disclosure, the term "Software" or "Computer Program Product" or "Application Program Interface", maybe written or coded using a programming language, and stored using any type of non-transitory computer-readable medium or machine-readable medium well known in the art; and comprises computer program instructions adapted for execution by a hardware element, such as a processor, wherein the instruction comprises commands that when executed cause the processor to perform a corresponding set of commands. The Cloud-based sequence editing API may be written or coded using a programming language and stored using any type of non-transitory computer-readable media or machine-readable media well known in the art. Examples of Cloud-based sequence editing API in the present invention comprise any Database and API components, code, modules, programs, applications, computer programs, application programs, system programs, machine programs, and operating system software.

With continued reference to FIG. 1A, as used in this disclosure, the term "patient profile" as used herein comprises patient characteristics and status, e.g.: a patient's age, gender, disease and stage, genetic and proteomic data input into the platform of the present invention, etc.

With continued reference to FIG. 1A, as used in this disclosure, "PBIMA application" herein refers to the proprietary software run on the networked, computerized system of the present invention, which comprises a cloud-based secured encrypted platform with non-transitory computer-readable storage medium able to receive data input; and then compute the optimal peptides for use in a vaccine composition with self and/or neo-antigens that can elicit an effective therapeutic response (e.g. elicit CD4+/CD8+ cell modulation).

With continued reference to FIG. 1A, as used in this disclosure, the term "system" or "computer system" refers to all the hardware and software involved in conducting the methods disclosed herein, including local and remote computers and cloud based systems comprising: a cloud-based server, the cloud based server comprising one or more of a central processing unit (CPU) or a graphics processing engine (GPU); at least one application programming interface; and at least one online database. In an embodiment, "computer" also refers to any laboratory and/or bioinformatics machine and equipment, etc. well known in the industry, comprising at least one processor or microprocessor for computing and analyzing data that leads to design of the vaccine compositions of the present invention.

With continued reference to FIG. 1A, as used in this disclosure, the term "PBIMA platform" refers to the hardware architecture and associated software framework required to design and produce the customized vaccine compositions disclosed herein; and to computing services that are accessible to one or more client devices, and that are operable to provide access to a plurality of software applications related to the operations of databases of FIG. 1A. And the PBIMA system comprises a computing platform comprising at least one processor and a memory for computing a personalized vaccine composition using the hardware and software, and vendors of FIG. 1A.

With continued reference to FIG. 1A, as used in this disclosure, the term "Payload" refers to an application program interface (API) that will connect the PBIMA pipeline with a Neo7Logix portal to input data, download data and access the pipeline analysis securely. Payload is also a filtered dataset to match the peptides for new design.

With continued reference to FIG. 1A, as used herein, the acronym "SMART" stands for S-strategic selection; M-molecular mapping; A-antigen alignment; R-recognition recognition; and T-tactical technology.

With continued reference to FIG. 1A, PBIMA is a biopathway HLA affinity mapping and selection prediction ranking device that combines biological intelligence programming, termed molecular mapping, applications of knowledge-based systems, artificial intelligence, and machine learning. The platform can utilize all next-generation sequencing (NGS) data, including whole-exome sequencing (WES), whole-genome sequencing (WGS), circulating DNA (ctDNA and cfDNA), NGS transcriptome analysis (RNAseq), and urine proteomics.

With continued reference to FIG. 1A, PBIMA is an In-Silico program that supports the paperless documentation and management of complex distributed processes (e.g., Patient data/peptide design Management). Tools include user interface, backend, requirements capture, and demonstration software (e.g., non-transitory computer-readable storage medium), deployed using AWS (Amazon Web Services™) high-speed processing core i.e., 96 or more but not limited to, and Biovia DS Pipeline 3DS services.

With continued reference to FIG. 1A, in an embodiment, the PBIMA method and system is applicable for cancer, autoimmune, and neurodegenerative diseases. Next, a precision mapping, ranking, and selection profile generates a precision-based personalized immuno-molecular augmentation (PBIMA) to reprogram the immune system to kill malignant cells. Of note, PBIMA, can also predict "best fit" drug therapy and nutritional supplements i.e., natural agents, botanical drugs, bioagent, nutraceuticals for many diseases.

With continued reference to FIG. 1A, PBIMA processes are represented as "Online mapping, ranking and selection", where "patient/doctors/PBIMA-Admin" communicate online, through the Internet.

With continued reference to FIG. 1A, for each PBIMA role, PBIMA serves as a guide for each part (i.e. Output): 1) identification of self-antigens and neo-antigens for CD4+/CD8+ cell modulation from cancer patient genome; 2) identification of self-antigens and neo-antigens for CD4+/CD8+ cell modulation from a patient with autoimmune disease; and 3) ranking peptides for PBIMA using a combination of patient transcriptomics and proteomics data, literature data, cancer hallmark collection, and manufactureability.

With continued reference to FIG. 1A, the PBIMA platform will utilize all next-generation sequencing (NGS) data, including whole-exome sequencing (WES), and whole-genome sequencing (WGS), to design the SOLVx™ therapeutic vaccine. This technology is a gene-protein-cell communication network editing interface and viral kinetic HTS screening that finds the virus-host to human mutations for real-time surveillance and rapid recognition. The PBIMA platform finds the viral mutations and designs the peptide vaccine for patients, a new vaccine.

With continued reference to FIG. 1A, in this emerging solution for novel pathogens and unknown pathogens, blood samples are collected from a set of infected living patients and infected deceased patients; and whole-exome sequencing (WES) is performed. The data from infected and dead patients is considered as separate cohorts. According to the requirement, the PBIMA system calculates and reads patient output data from WES (as 100x to more than 600x according to requirement). This solution provides high precision for dealing with mutation shifts in a pathogen outbreak. The vaccine treatment also outlines integrative options as treatment alternatives for a pandemic such as Disease-X, an unknown pathogen.

With continued reference to FIG. 1A, the pipeline of FIG. 1A utilizes the PBIMA design approach to determine the existing broad-spectrum anti-viral sequence from the patient sample.

With continued reference to FIG. 1A, the PBIMA method, system, and vaccine compositions of the present invention are suitable for administration to patient's having been diagnosed with or genetically predisposed to various disease states such as: a) Cancers: PBIMA can design all types of cancer vaccine but not limited to Multiple Myeloma, Melanoma, Breast Cancer, Colon Cancer, Lymphoma, Leukemia, Lymphoplasmacytic Lymphoma, Pancreatic Cancer, Lung Cancer, Bladder Cancer, Thyroid Cancer, and Brain Cancers. b) Autoimmune Disease and Inflammation-driven: PBIMA can design all types of Autoimmune and inflammation-driven diseases but not limited to Multiple Sclerosis (MS), Systemic Lupus Erythematosus (SLE), Amyotrophic Lateral Sclerosis (ALS), Scleroderma, Mixed Connective Tissue Disease, Hashimoto's Thyroiditis, Rheumatoid Arthritis, and Autoimmune-Related Inflammation. c) Neurodegenerative Disease: PBIMA can design all types of neurodegenerative diseases vaccine but not limited to Alzheimer's Disease, Parkinson's Disease, Dementia, Brain Inflammatory Disease, CNS Degenerative Inflammation. d) Pathogen related infectious disease including virus, bacteria, fungus, parasites with identified strains, but not limited to COVID-19, Crimean-Congo haemorrhagic fever, Ebola virus disease and Marburg virus disease, Lassa fever, Middle East respiratory syndrome coronavirus (MERS-CoV) and Severe Acute Respiratory Syndrome (SARS), Nipah and henipaviral diseases, Rift Valley fever, Zika, "Disease X".

With continued reference to FIG. 1A, FIG. 1A is an exemplary Cloud-based sequence editing system architecture of the present invention with one or more PBIMA application program interfaces (APIs) and high speed 96 core or more core Cloud API to carry out the following functions, comprising: bio-banking, patient sample process, platform login with HL7 interface, process status, and Neo7Logix™ PBIMA vaccine design platform.

With continued reference to FIG. 1A, in an exemplary embodiment, the system architecture comprises, for example: 1) a bio-bank 102 storing samples of a patient's blood, tissue, and tumor; 2) the PBIMA platform 104 for logging into the system to input or import patient data and output vaccine sequences; 3) at least one remote computer 106 of a patient, physician, medical institution that can log into the PBIMA platform 104 via a wired and wireless network 103; 4) a Next-Generation Sequencing (NGS) OMICS file processing unit or module 108 for receiving and processing data input from e.g., bio-banking 102 of the patient sample; third party computer 106 with access to import data comprising one or more of—blood whole WES (FIG. 2, 210), tumor WES 220, tumor RNA 230, and urine proteomics 240; 5) a Susceptibility Tool (an open-source database and online API) 112 for generation a patient susceptibility map, which is an HLA alleles set; 6) a Peptide Analysis Tool 114 [e.g. a PBIMA Unification application program interface (API) (Neo7Logix™ Cloud-based integrative API)] for designing and ranking neoantigens of the 9-aminoacid peptides-MHC-I and 12-aminoacid peptides; and MHC-II i.e. small peptide to medium sequence peptides; 7) a Gene-Protein Editing Tool 116 (an open-source database and online API), such as for CRISP editing (see FIG. 3); 8) a Genome Uniqueness Tool 118 (an open-source database and online API), for aligning the uniqueness of the sequence. 9) a Gene-Protein-Disease Interaction Database 113 (an open-source/customized-SMART™ database and online API), 10) a Sequence Integrity (open source database and online API, Peptide physicochemical calculator, Thermofisher™, Dosorio R™ package) for receiving input from database 113 and tool 118, to optimize ranking with disease hallmarks (for target-based design); 11) a Payload API 122 to match the best payloads for delivery for more specific targeted delivery. 12) a PBIMA ranking tool 124 for integrative API) to design and rank neoantigens of the 9-aminoacid peptides-MHC-I, and 12-aminoacid peptides-MHC-II; 13) a peptide sequence manufacturing facility and computer 126 for producing a patient's customized vaccine composition, which if the sequences are rejected (e.g., due to non-potent, non-manufacturable, highly toxic etc), the ranking is recomputed at 124 and remanufactured.

With continued reference to FIG. 1A, in an embodiment, one or more PBIMA applications performs the primary computations of the present invention resulting in data input and the vaccine output; but, if the NGS vendor cannot provide VCF Files, then the PBIMA application further comprises a proprietary Unification API processing program to convert or prepare the necessary files for input. The non-transitory computer-readable medium further comprises a PBIMA Unification code to design and rank a plurality of neoantigens of about or exactly 9-amino acid peptides-MHC-I and about or exactly 12-amino acid peptides-MHC-II.

Figure 2:
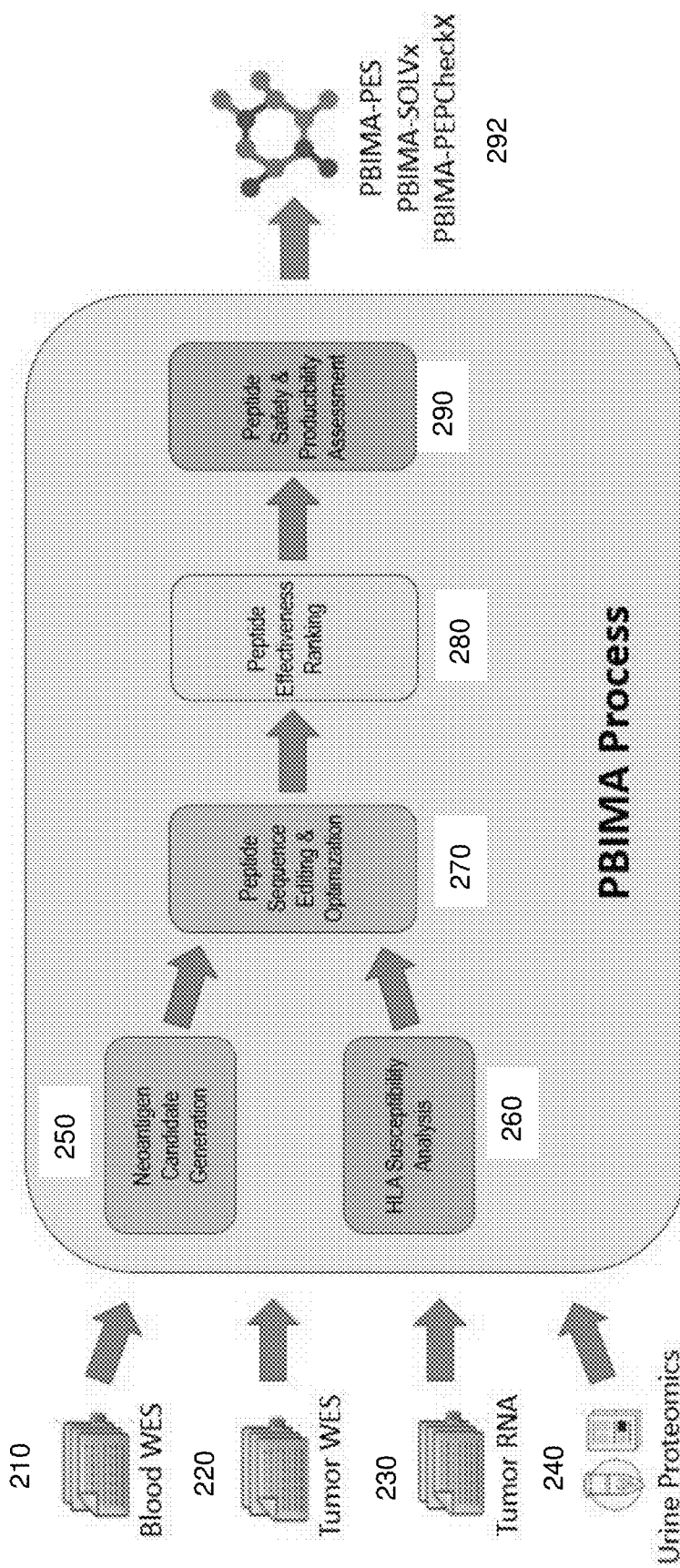
FIG. 2 is a diagram illustrating an exemplary embodiment of a PBIMA design technology consistent with the computational pipeline for PBIMA design.

Now referring to FIG. 2, an exemplary embodiment of a PBIMA design technology consistent with the computational pipeline for PBIMA design is illustrated. A simplified method for inputting a patient's data into the PBIMA platform 292, comprising: blood WES 210; tumor WES 220; tumor RNA 230; and urine proteomics 240. The PBIMA platform then determines the neoantigen candidate generation 250 and the HLA susceptibility analysis 260. This data is then used by the PBIMA platform to edit and optimize (filter and ranking) peptide sequences 270, then rank the peptides according to therapeutic efficacy 280, and produce and evaluate a vaccine comprising the highest ranked peptides 290.

Example: Lung Cancer Patient

Table 1 discloses PBIMA designed neoantigens (proteins) and Immunopeptide sequences for a Lung Cancer patient diagnosed using the computerized system and the present invention method. Final selection of proteins was sorted according to their rank and their peptide with the best affinity towards the patient's MHC1 complexes.

TABLE 1

| Protein | SEQ ID NO: | Sequence |
|---|---|---|
| NCAM1 | 1 | ATGGVSILK |
| PTPN11 | 2 | YINANIIML |
| SEMA5A | 3 | ISYKEIGLW |
| KRT5 | 4 | FSASSGLGL |
| GRIN2B | 5 | ISAQTVTPI |
| CYP2E1 | 6 | RFGPVFTLH* |

* Normal or Light font is good binding affinity, and bold type is weak to no binding affinity The following criteria accomplish HLA epitope prediction and ranking:
 1. Strongest Binding Affinity in one HLA Class
 2. Strongest/Med Binding Affinity to identical peptide sequence within multiple HLA classes
 3. Binding Affinity Averaging selection based upon the top average
 4. Structural considerations for HLA-peptide-T-cell receptor complex assembly Note: Immunopeptides were selected based upon the following criteria and not upon HLA binding affinity alone:
1. HLA Affinity Ranking
2. Biological Pathway Ranking
3. Association with Specified Cancer Risk In Population
4. Literature Support
5. Pivotal Molecular Protein to Protein Interactions and Cross Talk (PPI-CT) in Immune Augmentation
6. Antigen Integrity and Sequence Viability (Antigen/ Synthesis Analyzer)

Clarification on Ranking: Reds were selected based upon criteria 2-6 and will be noted as self-antigens externally synthesized and introduced as foreign epitopes for specified influences on Immuno-molecular controls on receptor signaling, sensitization, or blockade.

Peptide Pool Manufacturing Criteria
Peptide QC tests for the manufacturer:
Identity test: MS+HPLC
Water content test<10%
Solvent residue test<0.05%
Endotoxin test<0.3 IU/mg
Additional Criteria:

Peptide Sequences: On average, there are 10-20 9-amino acid (9 mer) peptides, requiring the following QC tests on them as listed above. Some tests are run on an entire mix (pool) of peptides to decrease the amount of material needed:

Cost Reduction: possible by combing solvent residue analysis with MS or HPLC to reduce cost.

Quantity: 100 mg of each sequence per patient is required.

Logistics: The objective is to reduce the cost of the final product and also meet requirements. Again, to meet logistic expectations of quick TAT, transit, and final packaging with high-quality peptide product.

Nano-Adjuvant Requirements: MF59 and CPG-ODI.

Example-Liver Cancer Patient

Table 2 is a PBIMA designed neoantigens (proteins) and self-antigens (proteins) and Immunopeptide sequences for a liver cancer patient diagnosed with us. Final selection of proteins sorted according to their rank and their peptide with the best affinity towards the patient's MHC1 complexes.

TABLE 2

| Protein | SEQ ID NO: | Sequence* | Antigen type |
|---|---|---|---|
| ARHGEF19 | 7 | SVEMSGDRM | neoantigen |
| CREB1 | 8 | GVPRIEEEE | neoantigen |
| RASAL1 | 9 | NVRLVEGRA | self-antigen |
| STARD13 | 10 | TLDFESNSV | neoantigen |
| SYNE1 | 11 | RSKTPTGLE | self-antigen |
| TRIOBP | 12 | ELDCRDLLG | neoantigen |

* Normal or Light font is good binding affinity, and bold type is weak to no binding affinity The following criteria accomplish HLA epitope prediction and ranking:
1. Strongest Binding Affinity in one HLA Class (immune Epitope Database (IEDB) is a free online resource funded by NIAID, NIH, USA)
2. Synthesis/Purification easiness (Synthesis Analyzer)
3. Solubility (Synthesis Analyzer)

Note: Immunopeptides were selected based upon the following criteria and not upon HLA binding affinity alone:
1. HLA Affinity Ranking-Immune Epitope Database (IEDB) is a free online resource funded by NIAID, NIH USA
2. Biological Pathway Ranking-Gene-Protein-Disease Interaction Database
3. Association with patient cancer risk in population-dbSNP from NCBI, NIH USA
4. Literature Support-Gene-Protein-Disease Interaction Database
5. Pivotal Molecular Protein to Protein Interactions and Cross Talk (PPI-CT) in Immune Augmentation Recommended Peptide QC Tests for the Manufacturer:
Identity test: MS+HPLC
Water content test<10%
Solvent residue test<0.05%
Endotoxin test<0.3 IU/mg Adjuvants approved for use in humans: Polyinosinic-Polycytidylic Acid Injection, South Land Pharmaceuticals, China Recommended Nano-Adjuvant previously used in human clinical trials or vaccines: Hiltonol, AddaVax, Quil-A®

Other similar adjuvants: VAdv-Ly0061

Administration: Recommended maximum dose for each peptide is 1 mg-4 mg/ml dose. Peptides can be pooled together in one immunopeptide pool. Vaccine adjuvant addition is advised for activation of sequences for immune induction and regulation. During the first 3 days of the immunopeptide pool, the patient tolerance dose has to be determined by a gradual increase to the full dose while observing reactivity. An initial test dose of 0.3 mg per peptide should be applied first to determine patient tolerance. After test dose subsequent dosing should be raised 0.25-0.5 mg/ml until top dose is achieved. Titrated dosing can be performed over three days to observe tolerance. When top dose is reached, then administration of the maximum dose continues for 17 consecutive days after that.

Total time of PBIMA administration is 20 days. PBIMA administration can be repeated for 3-4 cycles over 18 months if tumor regression is not observed. Cycles 1-2 can be 6-8 weeks apart and cycles 3-4 can be 12 weeks apart. Cycles 3-4 can be extended for longer than 20 days within the 18-month treatment window. Treatment window and cycling can be adjusted depending upon response to therapy, improvement in clinical signs, symptoms, improved quality of life based upon screening and follow up diagnostic serology, pathology and imaging, as well as, evidence of regression of cancer, tumor, proliferation, metastasis and overall cancer burden.

In case of PBIMA treatment of autoimmune and neurodegenerative disorders, disease regression is measured by reducing related destructive inflammation. It can be confirmed by screening, diagnostic and follow-up criteria, and improved clinical signs, symptoms, and quality of life observed.

Routes of administration: Determination of administration routes is subject to allowances in the physician/healthcare practitioner's scope of practice. By way of non-limiting examples, routes of administration of the vaccines disclosed herein comprise: direct site injection (e.g. into tumor); intramuscular injection; intravenous; oral; buccal; subcutaneous; sub-dermal; intranasal; intratumoral but not limited to parenteral (intravenous, intramuscular, and subcutaneous), oral, nasal, ocular, transmucosal (buccal, vaginal, and rectal), and transdermal.

Example: Progressive CNS Inflammation Autoimmune Disease Patient

Table 3 lists the PBIMA designed neoantigens (proteins) and self-antigens (proteins) and Immunopeptide sequences for a Progressive CNS Inflammation Autoimmune Disease patient diagnosed and treated using the present invention method and system. The final selection of proteins was sorted according to their rank and their peptide with the best affinity towards the patient's MHC-I complexes.

TABLE 3

| SEQ ID NO: | Autoimmune peptide sequences |
|---|---|
| 13 | WSREEQEREE |
| 14 | ADIYTEEAGR |
| 15 | NAPVSIPQ |
| 16 | SALLRSIPA |

Example: Progressive CNS Inflammation Autoimmune Disease Patient

Table 4 lists of PBIMA designed neoantigens (proteins) and self-antigens (proteins), and Immunopeptide sequences for another Progressive CNS Inflammation Autoimmune Disease patient diagnosed and treated using the present invention method and system. The final selection of proteins was sorted according to their rank and their peptide with the best affinity towards the patient's Citrullinated MEW Class-II complexes.

TABLE 4

| SEQ ID NO: | Protein | Sequence |
|---|---|---|
| 17 | MBP-R25 | YLATASTMDHA(cit)HGFLPRHRDTG |
| 18 | MBP-R49 | LDSIGRFFGGD(cit)GAPKRGSGKVP |
| 19 | MBP-R122 | DENPVVHFFKNIVTP(cit)TPPPSQGKGRG |
| 20 | MBP-R130 | PRTPPPSQGKG(cit)GLSLSRFSWGA |
| 21 | MBP-R122/R130 | P(cit)TPPPSQGKG(cit)G |

Progressive CNS Inflammation Autoimmune Disease patient

Note 14: MBP-R122 9mer fragment of citrullinated sequence portion affinity prediction completed by IEDB and PBIMA Citrullinated Fragment Sequence Location Selection. All sequences are predicted and ranked by Neo7Logix Platform as noted above.

Vaccine Adjuvants: Squalene/Oleic Acid naturally increase IL10. These adjuvants are indicated in autoantigen-related inflammation.

Additional Notes: Piceatannol (Kershaw and Kim, 2017), can inhibit ADAMTS4. Piceatannol is a metabolite of resveratrol found in red wine, grapes, passion fruit, white tea, and Japanese knotweed (amazon.com).

Integrative IV Design: Two Part IV design should include (12 week Design and Evaluate):

Part 1 (Beginning of week): Low dose dilute Sodium bicarbonate/DMSO/Low Dose Selenium slow intravenous drip (2 hours)

Part 2 (End of the week): Vitamin C (Casava Root) with Regulatory Cytokines (Biological IL-10) with very low dose Dexamethasone slow intravenous drip (2 hours)

Injection Therapy: Glucosamine Sulfate/Boron/Traumeel Injection 2X weekly

Antibiotic Therapy: Low Dose Intermittent Doxycycline/Minocycline to inhibit MMP2/9 neurodegenerative related inflammation (4 weeks on 3 weeks off for 3 cycles) (Rosenberg, 2015; Zhang et al., 2011)

Example: Novel Pathogen Treatment with Exemplary Sequences

Table 5 comprises a plurality of novel polypeptide vaccine sequences for treatment of a virus; and a vaccine composition comprising one or more of sequences of Table 3, wherein the composition may further comprise a pharmaceutically acceptable carrier or diluent.

TABLE 5

| SEQ ID NO | Pathogen Peptide Sequences |
|---|---|
| 22 | KAISFATTL |
| 23 | MAICGMNPI |
| 24 | KTFPPTEPK |
| 25 | YLYALVYFL |

The present invention further comprises one or more of:
a) an isolated polypeptide sequence produced by the present invention system, having at least 70% identity to the sequences provided herein.
b) an isolated polynucleotide (DNA) sequence having at 75%, 80%, 85%, 90%, 95%, or 100% sequence identity to any one of the polypeptide or polynucleotide sequences disclosed herein in Tables 1-3.
c) a host cell comprising polynucleotide sequences encoding any one of the polypeptide sequences produced by the present invention system, and further comprising a promoter suitable for expression of the sequences in vitro or in vivo.
d) one or more isolated polynucleotide sequences encoding any one of the polypeptide sequences produced by the system of the present invention; an isolated nucleic acid molecule, which encodes an amino acid sequence with at least 70% identity to any one of the amino acid sequences provided in the present invention (e.g. Table 5).
e) an isolated polypeptide sequence having at 75%, 80%, 85%, 90%, 95%, or 100% sequence identity to any one of the polypeptide or polynucleotide sequences disclosed herein.
f) a kit comprising one or more of (a-e);
g) an assay comprising one or more of (a-e);
h) an antibody or fragment thereof that specifically binds to one or more polypeptides disclosed herein, and/or produced by the method disclosed herein; and a vaccine comprising the antibody or fragment.
i) an immunogenic composition comprising one or more of (a-h); further comprising a pharmaceutically acceptable: adjuvant, and/or a carrier, and/or a diluent.
j) as claimed herein, all isolated nucleotide, polynucleotide sequences encode complementary DNA, and not genomic DNA.

Figure 1B:
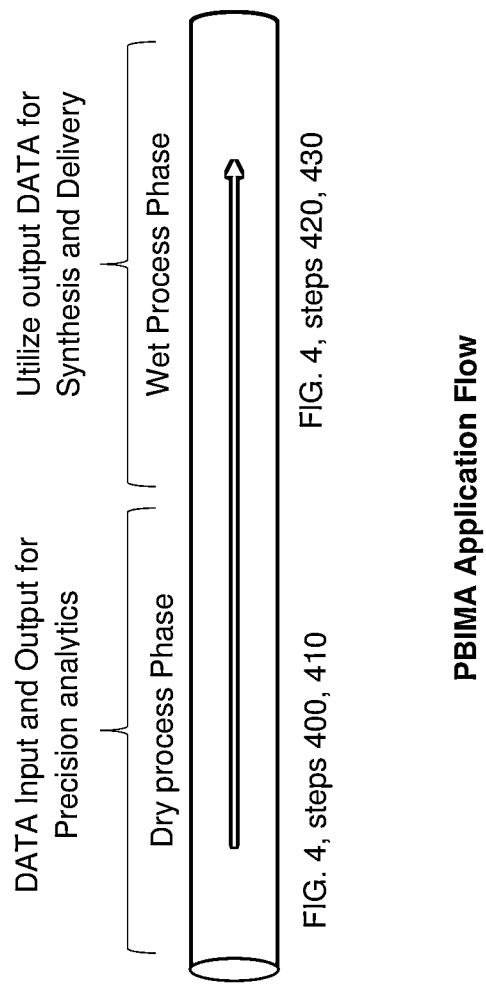
Figure 3:
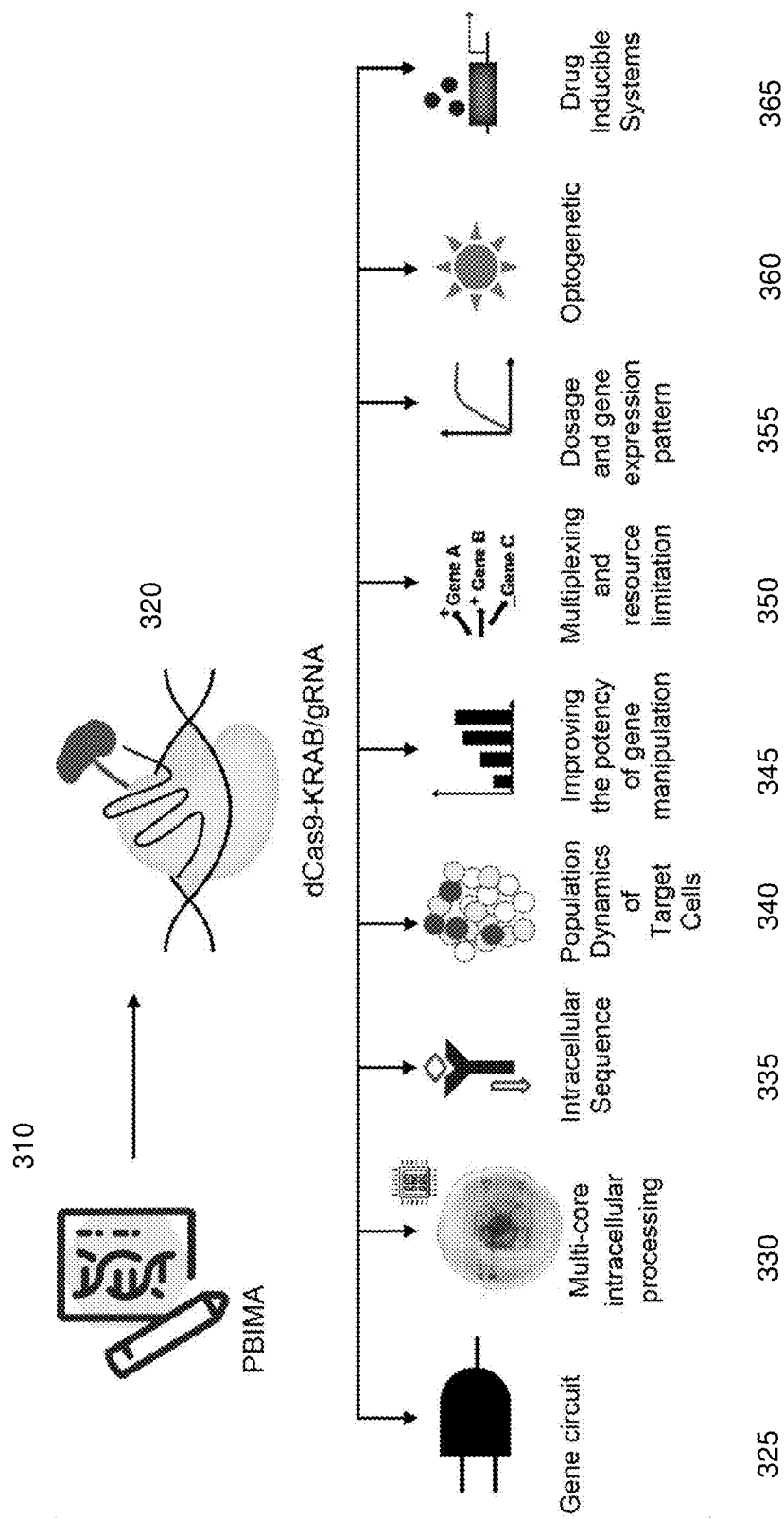
FIG. 3 illustrates a role of a PBIMA integrated CRISPR-cas system in the different biological applications.
Figure 4:
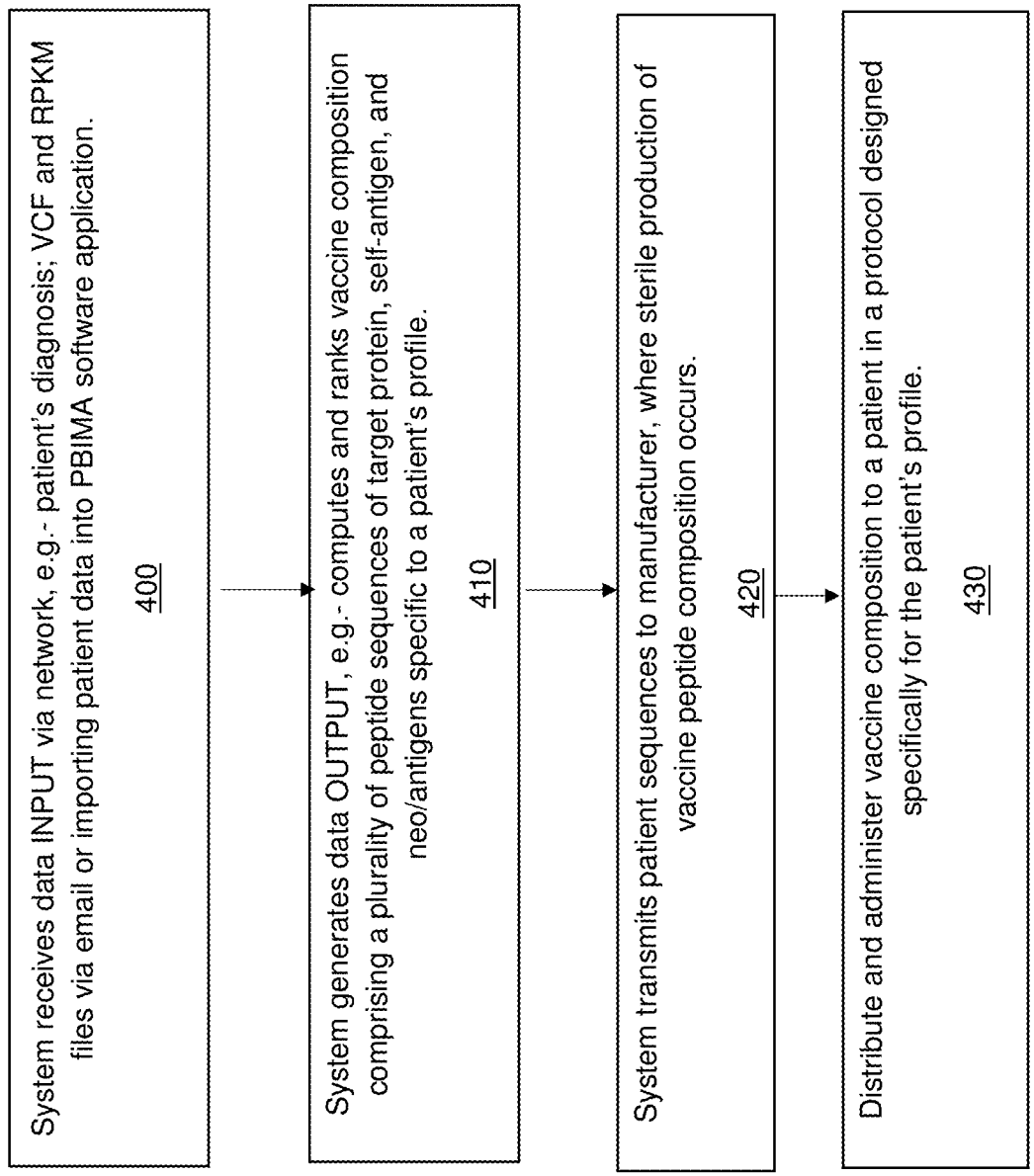
FIG. 4 is a flowchart of the four general steps taken to design a personalized vaccine using the PBIMA networked computer system and software, producing the vaccine, and treating a patient via administering the vaccine.

Now referring to FIG. 4, a flowchart of designing a personalized vaccine using the PBIMA networked computer system and software, producing the vaccine, and treating a patient via administering the vaccine is illustrated. The Personalized Immunotherapy of the present invention is a simple process that individualizes patient treatment to program his/her immune system to fight and regulate against disease. A high-level flowchart of the general steps in carrying out the computer method and system of FIGS. 1A-3. As illustrated in FIG. 1B, the PBIMA computerized Cloud-based sequence editing method comprises two phases, phase 1 is the Dry Lab process, and Phase 2 is the Wet Lab process. In Phase 1, the platform (FIG. 1A) automatically handles input of NGS, WES, RNAseq, and Urine proteomics data into the PBIMA application of the present invention (i.e. non-transitory computer readable storage medium) for neoantigen ranking and selection, which is used to design the personalized edited sequence or peptide or vaccine design data (e.g. see also FIG. 4, steps 400, 410). In phase 2, platform 104 utilizes the output data from phase 1. And in phase 2, the designed data for therapy is transferred to a wet lab for synthesizing the personalized vaccine; and for administration by the patient's clinician (e.g., see also FIG. 4, steps 420, 430).

With continued reference to FIG. 4, the patient's clinician(s) obtains samples from a patient, which requires collecting blood, urine, and tissue; or the use of existing stored tissue in the hospital/NGS vendors. This data is sent to a laboratory by the clinician or the system managers in step 400 where genetic and protein analysis is completed. All data is packaged for precision mapping, which is the second step 410. For example, as illustrated in FIG. 1A, a clinician or lab to which s/he has provided patient samples, imports or uploads a patient's NGS OMICS data 108 comprising VCF files into the PBIMA user interface 104 (e.g., a secure website). The system 100 then computes the ranked neo-antigens using the Susceptibility Tool 112, and the Peptide Analysis Tool 114, which comprises: MEW Class II prediction DB; IEDB,; and outputs peptide sequences of about 10-20 amino acids in a TSV file or other file formats. System 100 then performs CRISPR editing 116 on the 10-20 amino acid sequences. As illustrated in the networked computer system FIG. 1A, and the high-level illustration of FIG. 2, the first method step 400 of FIG. 4 is the input of data files into the PBIMA Cloud-based sequence editing API system 100 over the network 103 for the PBIMA application processing. PBIMA Cloud-based sequence editing API system 104 and proprietary API application utilizes the data that is coming from the hospital/physician's lab/vendors, so they do not need to prepare the patient's body samples to process the NGS/WES, RNAseq, urine proteomics steps analysis. NGS providers also deliver fastaq and bam files containing raw sequencing data. The fastaq files are huge and are needed. NGS data is imported into PBIMA Application system first for analysis, then results from PBIMA are used as output for the Phase 2 process. PBIMA uses sequences data and these need to be data cataloged to organize efficiently. A script (command text) takes VCF file with variations found in normal blood and tumor and finds sequences around somatic mutations. This is an input data. PBIMA application needs to input WES data from NGS vendor and what genomics analysis patients will afford to do through their hospital/physicians. The starting point is NGS OMICS Proteomics (Patient Data) flows to Final Design PBIMA Manufacturing and Delivery. PBIMA application does not require other tools and biological sample processing steps and guidelines as long as NGS vendor provides VCF file. If a NGS vendor cannot provide VCF Files, PBIMA application has its Unification API processing program to convert or prepare the necessary file for input.

With continued reference to FIG. 4, a patient's data is received from testing laboratories and the data is inputted into a sophisticated mapping and selection system (and application, where all data is analyzed and ranked according to the status of a patient's immune defense and regulation and specific to the disease process the patient's body is experiencing. A precision design comprising a vaccine composition comprising a plurality of peptides encoding antigens to stimulate the patient's immune system to fight the disease is then engineered from this analysis called PBIMA. PBIMA is Precision-Based Immuno-Molecular Augmentation, which simply means an immune sequence design aimed at correcting faults, initiating or regulating pathways as revealed by the patient's data that needs correction or enhancement. As further illustrated in FIG. 1A, the PBIMA vaccine platform and a plurality of software further comprise a NGS OMICS file processing unit or module for receiving and processing data input from (Bio-banking of patient samples), (clinician with access to platform 100 via HL7 Interface), computers, e.g.: (Blood & RNA tumor VCF file, WES VCF file from computer); Proteomics data excel file from computer; Peptide Analysis Tool (open-source online Database and API/software) and Susceptibility Tool (open-source online Database and API/software) on computer; Genome Uniqueness Tool (open-source online Database and API/software) on computer; Gene-Protein-Disease Interaction Database (Open source/customized online Database and API) on computer; Sequence Integrity (open-source online Database and API/software, Peptide physicochemical calculator) on computer; and PBIMA Unification data analyzing tools with API (Neo7Logix Cloud-based online Database and API run on the cloud not in a personal computer) to design and rank neoantigens of the 9-amino-acid peptides-MHC-I and 12 or 14-aminoacid peptides-MHC-II (peptides could short to medium 10 to 20) for the manufacturing). In step 410, the Cloud-based computerized system outputs, for example, 1) the identification of self-antigens and neo-antigens for CD8+ cell modulation from cancer patient genome; 2) identification of self-antigens and neo-antigens for CD4+ cell modulation from a patient with autoimmune disease; and 3) ranking peptides for PBIMA using a combination of patient transcriptomics and proteomics data, literature data, cancer hallmark collection, and manufacture-ability.

With continued reference to FIG. 4, upon completion of precision mapping, ranking, and selecting of a patient's data and unique design, then the present invention's PBIMA system packages (means patient's service including the vaccine delivery) the patient's sequences and delivers them to a certified personalized peptide manufacturer (in an Excel file format the final sequences). The peptide manufacturing is completed to cGMP quality (high purity/sterility) and unique to the patient's immune compatibility and programming to correct underlying faults and enhance better immune communication to fight and eradicate the patient's disease.

With continued reference to FIG. 4, the patient's personalized vaccine composition design is delivered to their physician/healthcare practitioner in approximately 6-9 weeks from when the laboratory receives their sample for genetic and protein testing. The patient's vaccine is then mixed with immune activators or adjuvants, administered by injection for 20 days, and maybe repeated for 4 cycles 6-12 weeks apart over 18 months. The patient's physician/healthcare practitioner selects the appropriate administration route and monitors and follows up on their progress, which may require further imaging, blood testing, and other specified markers. The immunopeptides tailored for the patient are enough of a supply to administer for four cycles over 18 months. The peptide pools for the treatment course waiting to be used are stored at −20 to −80 degrees Celsius to keep them viable and well preserved while waiting to receive during the duration of the treatment course. The patient's physician/healthcare practitioner may also decide to integrate additional regenerative modalities, including integrative intravenous therapy, cell therapies, and other effective adjunctive treatments. The present invention further provides a protocol for proper handling and vaccine administration by physicians; and distributing the vaccines internationally safely. FIG. 3 is an illustration of the role of PBIMA integrated CRISPR tool in different biological applications. PBIMA platform 310 integrates CRISPR for more precise target identification and matching. Also, the CRISPR-cas/CRISPR-dcas system is highly productive when accompanied and integrated in PBIMA. It will optimize precision engineering and therapeutic targeting. PBIMA vaccine design is pooled with suitable CRISPR-dcas proteins. dCas proteins delivery along with PBIMA therapeutic design modulates the RNA or DNA functions in the patient. The dCas or Cas system consists of two major classes, six types and 33 subtypes. (e.g. Brezgin, Sergey; Kostyusheva, Anastasiya; Kostyushev, Dmitry; Chulanov, Vladimir. 2019. "Dead Cas Systems: Types, Principles, and Applications" Int. J. Mol. Sci. 20, no. 23: 6041.) In FIG. 3, the PBIMA platform 310 is used in combination with the CRISP system 320 (dCas9-DRAB/gRNA), and comprises: gene circuit 325; multi-core intracellular processing 330; intracellular sequence 335; population dynamics of target cells 340; improving the potency of gene manipulation 345; multiplexing and resource limitation; dosage and gene expression pattern; optogenetic; and inducible drug systems. This list of points comprises the functional activity of the CRISPR-cas system as implemented in the present invention. Delivery of the PBIMA in combination with cas system shows biological efficacy.

It is to be noted that any one or more of the aspects and embodiments described herein may be conveniently implemented using digital electronic circuitry, integrated circuitry, specially designed application specific integrated circuits (ASICs), field programmable gate arrays (FPGAs) computer hardware, firmware, software, and/or combinations thereof, as realized and/or implemented in one or more machines (e.g., one or more computing devices that are utilized as a user computing device for an electronic document, one or more server devices, such as a document server, etc.) programmed according to the teachings of the present specification, as will be apparent to those of ordinary skill in the computer art. These various aspects or features may include implementation in one or more computer programs and/or software that are executable and/or interpretable on a programmable system including at least one programmable processor, which may be special or general purpose, coupled to receive data and instructions from, and to transmit data and instructions to, a storage system, at least one input device, and at least one output device. Appropriate software coding may readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, Programmable Logic Devices (PLDs), and/or any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 5:
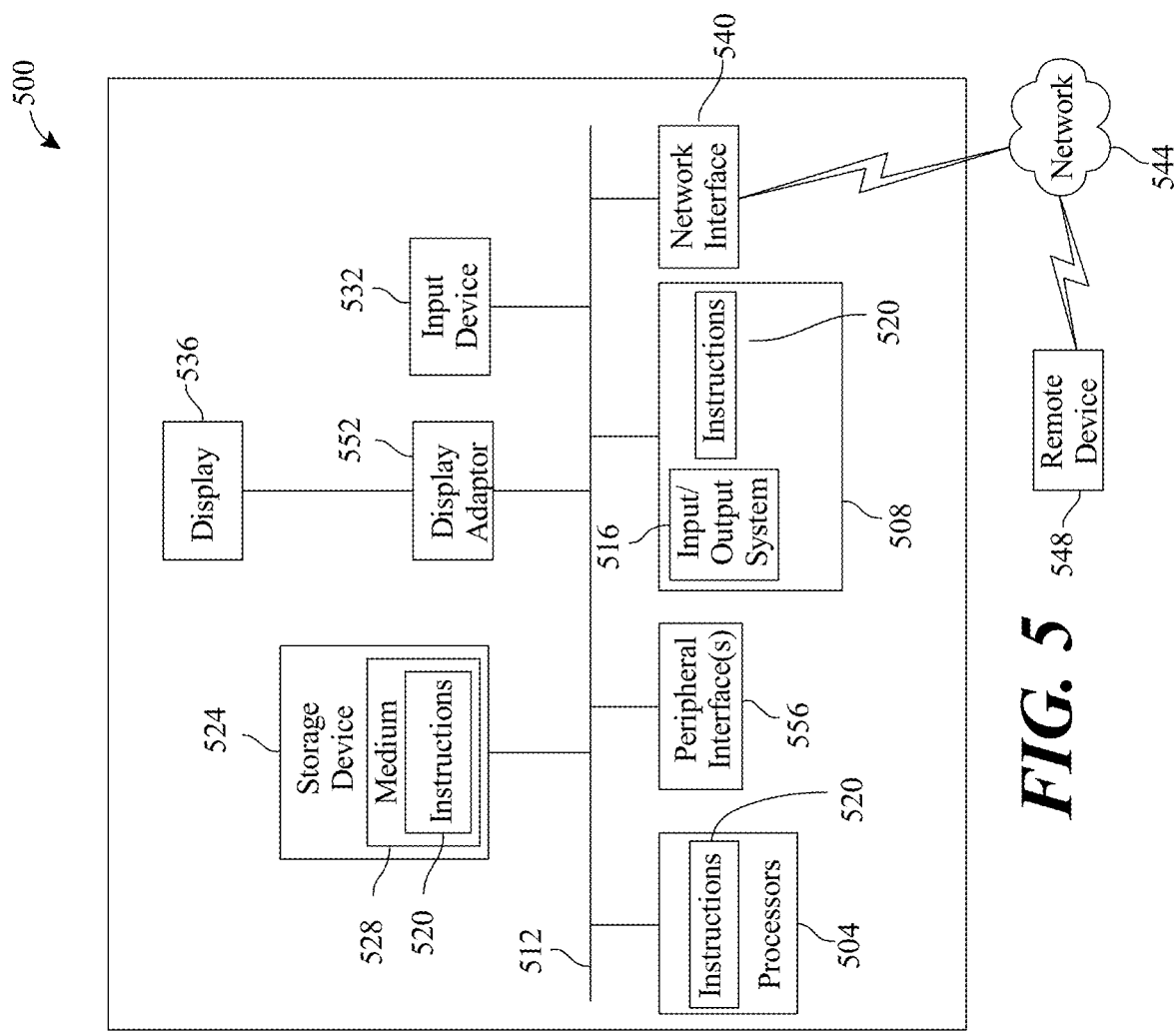
FIG. 5 is a block diagram of a computing system that can be used to implement any one or more of the methodologies disclosed herein and any one or more portions thereof.

FIG. 5 shows a diagrammatic representation of one embodiment of a computing device in the exemplary form of a computer system 500 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 500 includes a processor 504 and a memory 508 that communicate with each other, and with other components, via a bus 512. Bus 512 may include any of several types of bus structures including, but not limited to, a memory bus, a memory controller, a peripheral bus, a local bus, and any combinations thereof, using any of a variety of bus architectures.

Memory 508 may include various components (e.g., machine-readable media) including, but not limited to, a random-access memory component, a read only component, and any combinations thereof. In one example, a basic input/output system 516 (BIOS), including basic routines that help to transfer information between elements within computer system 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Computer system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with computer system 500 (e.g., via an external port connector (not shown)). Particularly, storage device 524 and an associated machine-readable medium 528 may provide nonvolatile and/or volatile storage of machine-readable instructions, data structures, program modules, and/or other data for computer system 500. In one example, software 520 may reside, completely or partially, within machine-readable medium 528. In another example, software 520 may reside, completely or partially, within processor 504.

Computer system 500 may also include an input device 532. In one example, a user of computer system 500 may enter commands and/or other information into computer system 500 via input device 532. Examples of an input device 532 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to computer system 500 via storage device 524 (e.g., a removable disk drive, a flash drive, etc.) and/or network interface device 540. A network interface device, such as network interface device 540, may be utilized for connecting computer system 500 to one or more of a variety of networks, such as network 544, and one or more remote devices 548 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 544, may employ a wired and/or a wireless mode of communication. In general, any network topology may be used. Information (e.g., data, software 520, etc.) may be communicated to and/or from computer system 500 via network interface device 540.

Computer system 500 may further include a video display adapter 552 for communicating a displayable image to a display device, such as display device 536. Examples of a display device include, but are not limited to, a liquid crystal display (LCD), a cathode ray tube (CRT), a plasma display, a light emitting diode (LED) display, and any combinations thereof. Display adapter 552 and display device 536 may be utilized in combination with processor 504 to provide graphical representations of aspects of the present disclosure. In addition to a display device, computer system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve embodiments as disclosed herein. Accordingly, this description is meant to be taken only by way of example, and not to otherwise limit the scope of this invention.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

```
                         SEQUENCE LISTING

Sequence total quantity: 25
SEQ ID NO: 1             moltype = AA   length = 9
FEATURE                  Location/Qualifiers
source                   1..9
                         mol_type = protein
                         organism = Homo sapiens
SEQUENCE: 1
ATGGVSILK                                                                  9

SEQ ID NO: 2             moltype = AA   length = 9
FEATURE                  Location/Qualifiers
source                   1..9
                         mol_type = protein
                         organism = Homo sapiens
SEQUENCE: 2
YINANIIML                                                                  9

SEQ ID NO: 3             moltype = AA   length = 9
FEATURE                  Location/Qualifiers
source                   1..9
                         mol_type = protein
                         organism = Homo sapiens
SEQUENCE: 3
ISYKEIGLW                                                                  9

SEQ ID NO: 4             moltype = AA   length = 9
FEATURE                  Location/Qualifiers
source                   1..9
                         mol_type = protein
                         organism = Homo sapiens
SEQUENCE: 4
FSASSGLGL                                                                  9

SEQ ID NO: 5             moltype = AA   length = 9
FEATURE                  Location/Qualifiers
source                   1..9
                         mol_type = protein
                         organism = Homo sapiens
SEQUENCE: 5
ISAQTVTPI                                                                  9

SEQ ID NO: 6             moltype = AA   length = 9
FEATURE                  Location/Qualifiers
source                   1..9
                         mol_type = protein
                         organism = Homo sapiens
SEQUENCE: 6
RFGPVFTLH                                                                  9

SEQ ID NO: 7             moltype = AA   length = 9
FEATURE                  Location/Qualifiers
source                   1..9
                         mol_type = protein
                         organism = Homo sapiens
SEQUENCE: 7
SVEMSGDRM                                                                  9

SEQ ID NO: 8             moltype = AA   length = 9
FEATURE                  Location/Qualifiers
source                   1..9
                         mol_type = protein
                         organism = Homo sapiens
SEQUENCE: 8
GVPRIEEEE                                                                  9
```

```
SEQ ID NO: 9            moltype = AA  length = 9
FEATURE                 Location/Qualifiers
source                  1..9
                        mol_type = protein
                        organism = Homo sapiens
SEQUENCE: 9
NVRLVEGRA                                                                 9

SEQ ID NO: 10           moltype = AA  length = 9
FEATURE                 Location/Qualifiers
source                  1..9
                        mol_type = protein
                        organism = Homo sapiens
SEQUENCE: 10
TLDFESNSV                                                                 9

SEQ ID NO: 11           moltype = AA  length = 9
FEATURE                 Location/Qualifiers
source                  1..9
                        mol_type = protein
                        organism = Homo sapiens
SEQUENCE: 11
RSKTPTGLE                                                                 9

SEQ ID NO: 12           moltype = AA  length = 9
FEATURE                 Location/Qualifiers
source                  1..9
                        mol_type = protein
                        organism = Homo sapiens
SEQUENCE: 12
ELDCRDLLG                                                                 9

SEQ ID NO: 13           moltype = AA  length = 10
FEATURE                 Location/Qualifiers
source                  1..10
                        mol_type = protein
                        organism = Homo sapiens
SEQUENCE: 13
WSREEQEREE                                                               10

SEQ ID NO: 14           moltype = AA  length = 10
FEATURE                 Location/Qualifiers
source                  1..10
                        mol_type = protein
                        organism = Homo sapiens
SEQUENCE: 14
ADIYTEEAGR                                                               10

SEQ ID NO: 15           moltype = AA  length = 8
FEATURE                 Location/Qualifiers
source                  1..8
                        mol_type = protein
                        organism = Homo sapiens
SEQUENCE: 15
NAPVSIPQ                                                                  8

SEQ ID NO: 16           moltype = AA  length = 9
FEATURE                 Location/Qualifiers
source                  1..9
                        mol_type = protein
                        organism = Homo sapiens
SEQUENCE: 16
SALLRSIPA                                                                 9

SEQ ID NO: 17           moltype = AA  length = 23
FEATURE                 Location/Qualifiers
source                  1..23
                        mol_type = protein
                        organism = Homo sapiens
SEQUENCE: 17
YLATASTMDH ACHGFLPRHR DTG                                                23

SEQ ID NO: 18           moltype = AA  length = 23
FEATURE                 Location/Qualifiers
source                  1..23
                        mol_type = protein
                        organism = Homo sapiens
```

```
SEQUENCE: 18
LDSIGRFFGG DCGAPKRGSG KVP                                          23

SEQ ID NO: 19          moltype = AA  length = 27
FEATURE                Location/Qualifiers
source                 1..27
                       mol_type = protein
                       organism = Homo sapiens
SEQUENCE: 19
DENPVVHFFK NIVTPCTPPP SQGKGRG                                      27

SEQ ID NO: 20          moltype = AA  length = 23
FEATURE                Location/Qualifiers
source                 1..23
                       mol_type = protein
                       organism = Homo sapiens
SEQUENCE: 20
PRTPPPSQGK GCGLSLSRFS WGA                                          23

SEQ ID NO: 21          moltype = AA  length = 13
FEATURE                Location/Qualifiers
source                 1..13
                       mol_type = protein
                       organism = unidentified
SEQUENCE: 21
PCTPPPSQGK GCG                                                     13

SEQ ID NO: 22          moltype = AA  length = 9
FEATURE                Location/Qualifiers
source                 1..9
                       mol_type = protein
                       organism = Homo sapiens
SEQUENCE: 22
KAISFATTL                                                           9

SEQ ID NO: 23          moltype = AA  length = 9
FEATURE                Location/Qualifiers
source                 1..9
                       mol_type = protein
                       organism = Homo sapiens
SEQUENCE: 23
MAICGMNPI                                                           9

SEQ ID NO: 24          moltype = AA  length = 9
FEATURE                Location/Qualifiers
source                 1..9
                       mol_type = protein
                       organism = Homo sapiens
SEQUENCE: 24
KTFPPTEPK                                                           9

SEQ ID NO: 25          moltype = AA  length = 9
FEATURE                Location/Qualifiers
source                 1..9
                       mol_type = protein
                       organism = Homo sapiens
SEQUENCE: 25
YLYALVYFL                                                           9
```

What is claimed is:

1. A precision-based immunomolecular augmentation (PBIMA) computerized method for designing and treating a patient with a customized therapeutic peptides or peptide vaccine, comprising:

receiving a data input, by a cloud-based system, of a patient data comprising one or more of: a patient transcriptomics data, and a patient urine proteomics data;

computing a precision data output, by the cloud-based system, of a vaccine composition comprising a plurality of ranked peptide sequences encoding self-antigens and/or neo-antigens for a CD4+/CD8+ natural killer (NK) cell modulation specific to a patient's profile, and able to elicit an effective therapeutic response against a patient disease;

computing a CRISPR prime editing and an intracellular multi-core processing on the vaccine composition to produce a DNA-RNA and epigenetic modulation plurality of immunopeptide sequences;

conducting an immunopeptide synthesis and manufacturing of the vaccine composition;

conducting the delivery of the vaccine composition to a patient's clinician or institution, and administrating the vaccine composition to the patient; and wherein the patient has been diagnosed with, and/or is genetically predisposed to one or more diseases comprising: a cancer, an autoimmune disease, a neurodegenerative disease, and/or a pathogenic infectious disease.

2. The PBIMA computerized method of claim 1, wherein computing a precision data output comprises one or more of:
identifying a plurality of therapeutic peptides, peptide vaccine, self-antigens and neo-antigens for the CD4+/CD8+NK cell modulation from:
a cancer patient genome;
a patient with an autoimmune disease;
a patient with a neurodegenerative disease,
a patient with a pathogenic infectious disease;
a patient's disease diagnostic reagents tagged with peptides;
ranking the plurality of therapeutic peptide sequences for the cloud-based system to use in the vaccine composition; and
wherein computing a CRISPR prime editing comprises the integration of PBIMA therapeutic vaccine ranked plurality of peptide sequences.

3. The PBIMA computerized method claim 1, further comprising: projecting a patient's OMICs data molecular profiling data onto a knowledgebase of one or more molecular interactions, functional associations, and mechanistic cancer models that have been compiled under different cancer hallmarks.

4. The PBIMA computerized method of claim 1, further comprising utilizing a programmed immunogenetic adaptation process knowledge for the patient's evolutionary regenerative adaptation or disease-free survival.

5. The PBIMA computerized method of claim 1, wherein the data analysis step further comprises one or more of: high-affinity profiling, matching and selecting of the plurality of peptide sequences based on a patient's immune compatibility, immune-editing ability, and adaptation process comprising system reproducibility, for treatment of a specific disease.

6. The PBIMA computerized method of claim 1, wherein a vaccine cost is controlled by increased precision of a peptide design, allowing for a smaller number of peptides in each vaccine or therapeutics.

7. The PBIMA computerized method of claim 1, further comprising a selection of a plurality of patients likely to respond to the vaccine composition using ex-vivo activation and expansion of a patient's T-cells.

8. The PBIMA computerized method of claim 1, wherein the vaccine composition comprises an efficacy of at least 60% for cancer or the disease that currently has no effective treatment or has been abandoned by standard-of-care and considered incurable.

9. The PBIMA computerized method of claim 1, wherein the cloud-based system comprises: a cloud-based server comprising one or more of a central processing unit (CPU) or a graphics processing engine (GPU); at least one application programming interface; and at least one online database; at least highest computing multi-core processor with at least a 96 cores.

10. The PBIMA computerized method of claim 1, further comprising conducting a genetic and protein analysis on a patient sample comprising one or more of: a fresh blood, a urine sample, a fresh tissue sample, or a stored tissue sample from a biobank.

11. A cloud-based computer system able to design a personalized peptide vaccine, comprising:
a precision based immunomolecular augmentation (PBIMA) computing platform comprising a plurality of online databases and application program interfaces (APIs), and comprising non-transitory computer readable storage medium storing computer-executable code comprising all of:
a next-generation sequencing (NGS) OMICS file processing unit comprising a Blood and RNA tumor VCF file, a WES VCF file, and a urine Proteomics data excel file;
a Peptide Analysis Tool comprising an open-source database and an online API
a Susceptibility Tool comprising an open-source database and an online API;
a Genome Uniqueness comprising an open-source database and an online API;
a Gene-Protein-Disease Interaction Database comprising an open-source or proprietary database and an online API;
a Sequence Integrity module comprising an open-source database and online API, Thermofisher, Dosorio R package);
PBIMA Unification API (Neo7Logix Cloud base integrative API) to design and rank neoantigens of the 9-aminoacid peptides-MHC-I, and 12-aminoacid peptides-MHC-II;
a Payload API to match the best payloads for delivery for a more specific targeted delivery;
a plurality of local and/or remote computers able to transmit patient input data to a PBIMA editing system, the input data comprising: NGS, WES, RNAseq, circulating DNA (ctDNA and cfDNA) and Urine proteomics data;
a wired and/or wireless network connecting local and/or remote computers' plurality;
wherein a patient has been diagnosed with, or is genetically predisposed to, a disease comprising: a cancer, an autoimmune disease, a neurodegenerative disease, or a pathogen related infectious disease; and
wherein the personalized peptide vaccine comprises a plurality of peptide sequences comprising about 5 to about 20 peptide sequences computed to be the most therapeutically effective peptide for treating the patient by eliciting a CD4+/CD8+NK cell modulation specific to a patient's profile.

12. The cloud-based system of claim 11, wherein the networked computer system's platform further comprises a gene-protein-cell communication network editing interface able to find one or more patient genetic mutations and predict a corresponding normal gene for the mutated genes in the patient.

13. A personalized peptide vaccine composition, comprising:
a plurality of peptide sequences encoding self-antigens and neo-antigens for a CD4+/CD8+ Natural Killer (NK) cell modulation specific to a patient's profile, and able to elicit an effective therapeutic response against a patient disease;
wherein a patient has been diagnosed with, or is genetically predisposed to, a disease comprising: a cancer, an autoimmune disease, a neurodegenerative disease, or a pathogen related infectious disease;
wherein the plurality of peptide sequences comprises about 5 to about 20 peptide sequences computed to be the most therapeutically effective for treating the patient; and
wherein the individualized therapeutic peptides or peptide vaccine composition is produced by:
receiving a data input, by a cloud-based system, of a patient data comprising one or more of: a patient transcriptomics data, and a patient urine proteomics data;

computing a precision data output, by the cloud-based system, of a vaccine composition comprising a plurality of therapeutic peptide sequences encoding peptides, self-antigens or neo-antigens specific to a patient's profile, and able to elicit an effective therapeutic response against a patient disease;

computing a CRISPR prime editing and an intracellular multi-core processing on the vaccine composition to produce a DNA-RNA and epigenetic modulation plurality of immunopeptide sequences; and conducting an immunopeptide synthesis and manufacturing of the vaccine composition.

14. The personalized peptide vaccine composition of claim 13, further comprising a pharmaceutically acceptable carrier, comprising one or more of Citrullinated peptide, Cyclodextrin, poly I:C, Squalene or DHA, phosphatidylcholine, wherein the carrier is selected by utilizing a Payload application program interface (API) to determine the best candidate carrier comprising one or more adjuvants.

15. The vaccine composition of claim 13, wherein the cancer disease comprises one or more of: Multiple Myeloma, Melanoma, Breast Cancer, Colon Cancer, Lymphoma, Leukemia, Lymphoplasmacytic Lymphoma, Pancreatic Cancer, Lung Cancer, Bladder Cancer, Thyroid Cancer, and Brain Cancers.

16. The vaccine composition of claim 13, wherein the Autoimmune Disease comprises one or more of: Multiple Sclerosis (MS), Systemic Lupus Erythematosus (SLE), Amyotrophic Lateral Sclerosis (ALS), Scleroderma, Mixed Connective Tissue Disease, Hashimoto's Thyroiditis, Rheumatoid Arthritis and Autoimmune-Related Inflammation.

17. The vaccine composition of claim 13, wherein the Neurodegenerative Disease comprises one or more of: Alzheimer's Disease, Parkinson's Disease, Dementia, Brain Inflammatory Disease, CNS Degenerative Inflammation.

18. The vaccine composition of claim 13, wherein a pathogen-related infectious disease comprises one or more of: virus, bacteria, fungus, parasites with identified strains.

19. The vaccine composition of claim 13, comprising one or more sequences having at least 90% sequence identity with a polypeptide sequence of Table 5.

* * * * *